US008017597B2

(12) United States Patent
Murofushi et al.

(10) Patent No.: US 8,017,597 B2
(45) Date of Patent: Sep. 13, 2011

(54) ANALGESIC AGENT COMPRISING CYCLIC PHOSPHATIDIC ACID DERIVATIVE

(75) Inventors: Kimiko Murofushi, Tokyo (JP); Harumi Kanashiki, Tokyo (JP)

(73) Assignee: Ochanomizu University, Tokyo (JP)

( * ) Notice: Subject to any disclaimer, the term of this patent is extended or adjusted under 35 U.S.C. 154(b) by 0 days.

(21) Appl. No.: 12/907,666

(22) Filed: Oct. 19, 2010

(65) Prior Publication Data

US 2011/0086820 A1    Apr. 14, 2011

Related U.S. Application Data

(62) Division of application No. 12/447,566, filed as application No. PCT/JP2007/001463 on Dec. 25, 2007, now abandoned.

(30) Foreign Application Priority Data

Dec. 28, 2006 (JP) .................................. 2006-353642

(51) Int. Cl.
*A61K 31/665* (2006.01)
(52) U.S. Cl. .......................................... 514/99; 514/101
(58) Field of Classification Search .......................... None
See application file for complete search history.

(56) References Cited

U.S. PATENT DOCUMENTS

| 6,914,056 B1 | 7/2005 | Shinitzky |
| 2004/0176329 A1 | 9/2004 | Murofushi et al. |
| 2004/0214799 A1 | 10/2004 | Mukai et al. |
| 2004/0220149 A1 | 11/2004 | Murofushi et al. |
| 2006/0122155 A1 | 6/2006 | Murofushi et al. |
| 2009/0326256 A1 | 12/2009 | Murofushi et al. |

FOREIGN PATENT DOCUMENTS

| EP | 1 386 612 | 2/2004 |
| EP | 1 391 204 | 2/2004 |
| EP | 1 162 959 | 3/2005 |
| JP | 05-230088 | 9/1993 |
| JP | 07-149772 | 6/1995 |
| JP | 07-258278 | 10/1995 |
| JP | 09-25235 | 1/1997 |
| JP | 2001-178489 | 7/2001 |
| JP | 2002-308778 | 10/2002 |
| JP | 2002-308779 | 10/2002 |
| JP | 2002-540146 | 11/2002 |
| JP | 2004-010582 | 1/2004 |
| WO | 00/57865 | 10/2000 |
| WO | 02/083148 | 10/2002 |
| WO | 02/083149 | 10/2002 |
| WO | 02/094286 | 11/2002 |
| WO | 03/104246 | 12/2003 |

OTHER PUBLICATIONS

Baker et al. Journal of Biological Chemistry, vol. 281, No. 32, pp. 22786-22793, Aug. 11, 2006.*
Murakami-Murofushi, K., et al., J. Biol. Chem., vol. 267, No. 30, pp. 21512-21517 (1992).
Murakami-Murofushi, K., et al., Biochem. Biophys. Acta, vol. 1258, pp. 57-60 (1995).
Kobayashi, T., et al., Life Sci., vol. 65, No. 21, pp. 2185-2191 (1999).
Murakami-Murofushi et al., "Biological functions of a novel lipid mediator, cyclic phosphatidic acid," Biochimica and Biophysica Acta, Molecular and Cell Biology of Lipids, Elsevier, Amsterdam, NL, vol. 1582, No. 1-3, pp. 1-7, 2002.
Uchida et al., "The effects of morphine on supraspinal and propriospinal somatocardiac reflexes in anesthetized rats," Neuroscience Letters, vol. 269, No. 3, pp. 161-164, 1999.
Hefti et al., "Novel class of pain drugs based on antagonism of NGF," Trends in Pharmacological Sciences, Elsevier, Hayworth, GB, vol. 27, No. 2, pp. 85-91, 2006.
Fujiwara et al., "Cyclic phosphatidic acid elicits neurotrophin-like actions in embryonic hippocampal neurons," Journal of Neurochemistry, vol. 87, No. 5, pp. 1272-1283, 2003.
Park et al., "Lipid mediators of sensitivity in sensory neurons," Trends in Pharmacological Sciences, Elsevier, 'Hayworth, GB, vol. 26, No. 11, pp. 571-577, 2005.
Extended European Search Report dated Jan. 25, 2010 that issued with respect to European Patent Application No. 07849882.1.
Mamillapalli et al., FEBS Letters, vol. 436 (1998), pp. 256-258.
Mukai et al., Int. J. Cancer: 81, (1999), pp. 918-922.
Baker et al., J. Biol. Chem. vol. 281, No. 32, pp. 22786-22793.
"Pain," Merck Manuals Online Medical Library: Home Edition. Accessed Mar. 24, 2009. <http://www.merck.com/mmhe/sec06/ch078/ch078a.html>.
Stillman, Mark "Clinical approach to patients with neuropathic pain," Cleveland Clinic Journal of Medicine, 73 (8), pp. 726-730, 733-739.

* cited by examiner

*Primary Examiner* — Rebecca Anderson
*Assistant Examiner* — Alicia L Otton
(74) *Attorney, Agent, or Firm* — Greenblum & Bernstein, PLC

(57) ABSTRACT

An object of the present invention is to elucidate an analgesic effect as one of new cPA bioactivities and thus to provide a novel analgesic agent. The present invention provides an analgesic agent which comprises a cyclic phosphatidic acid derivative that is one type of phospholipid.

4 Claims, 3 Drawing Sheets

ANALGESIC AGENT COMPRISING CYCLIC PHOSPHATIDIC ACID DERIVATIVE

CROSS-REFERENCE TO RELATED APPLICATION

This application is a divisional of application Ser. No. 12/447,566, which is a national stage of PCT/JP2007/001463, filed Dec. 25, 2007, which claims priority to Japanese Application No. 2006-353642, filed Dec. 28, 2006. The disclosures of application Ser. Nos. 12/447,566 and PCT/JP2007/001463 are incorporated by reference herein in their entireties.

TECHNICAL FIELD

The present invention relates to an analgesic agent comprising a cyclic phosphatidic acid derivative that is one type of phospholipid.

BACKGROUND ART

"Pain" treatment in Japan is said to be at a level lower than that in Europe and the United States. The environment in Japan for basic research concerning "pain" is greatly inferior to that in Europe and the United. States. Low social or governmental understanding concerning "pain" currently does not lead to "pain" treatment.

To improve medical care for "pain" by overcoming the current situation, activities should be promoted in Japan with cooperation among doctors in clinical practice, researchers involved in basic research, people involved in the government, and the like. There are many things that remain to be done including, in addition to an actual condition survey of "pain" treatment in Japan, efforts to examine effects on the social economy and the like, elucidation of the mechanism of "pain," development of forms of treatment, formulation of treatment guidelines, enhanced "pain" education in the field of education, and educational activity for general people and patients, for example. Also, in preparation for the aging society of the near future, establishment of medical care for "pain" is thought to be an urgent need. This will improve the quality of life of patients suffering from "pain" and reduce the burden of social cost for medical care. It will also suppress social labor productivity loss and improve the Japanese economy.

Known major analgesic agents are largely classified as narcotic analgesics or antipyretic analgesics. Narcotic analgesics mainly act on the central nervous system and have strong analgesic effects. Narcotic analgesics act on opioid receptors. Examples of such narcotic analgesics include weak opioids (e.g., codeine) having relatively weak analgesic effects and strong opioids (e.g., morphine) having strong analgesic effects, but having chemical resistance. On the other hand, aspirin, acetaminophen, ibuprofen, indomethacin, and the like are known as antipyretic analgesics, which act mainly on the peripheral nervous system, and have moderate analgesic effects. Antipyretic analgesics generally have anti-inflammatory effects and analgesic antipyretic effects via COX inhibition. Analgesic antipyretic drugs, such as acetaminophen, lacking COX inhibitory action also exist.

Meanwhile, the present inventors have conducted various cellular biochemical analyses using the true slime mold *Physarum polycephalum* as an experimental material. The true slime mold has been revealed to undergo morphological changes depending on changes in exterior environment and exert significant changes in the composition and metabolism of biomembrane lipids along with its proliferation and differentiation. As a result of the structural analysis of a novel lipid component isolated and identified from haploid myxoamoeba in 1992, the lipid component was confirmed to be a substance containing cyclopropane-containing hexadecanoic acid at position sn-1 of the glycerol backbone and phosphoric acids circularly ester-linked at positions sn-2 and 3 (Murakami-Murofushi, K., et al.: Jr. Biol. Chem., 267, 21512-21517 (1992)). This substance was named PHYLPA since it is an LPA analog derived from *Physarum*. PHYLPA suppresses the activity of DNA polymerase α of eukaryotic cells and is obtained from a lipid fraction in which the proliferation of cultured animal cells has been suppressed. PHYLPA has been confirmed to exhibit such bioactivities. PHYLPA has characteristic fatty acids. As a result of examining the bioactivities of structural analogs prepared via organic synthesis involving substitution of the fatty acid portions with other general fatty acids, physiological effects similar to those of PHYLPA were confirmed (Murakami-Murofushi, K., et al.: Biochem. Biophys. Acta, 1258, 57-60 (1995)). Accordingly, an important structure for these physiological effects is inferred to be a cyclic phosphate structure at glycerol positions sn-2 and 3. Lipids having such a structure are collectively referred to as cyclic phosphatidic acids (cPAs). Moreover, it was demonstrated that cyclic phosphatidic acids (cPAs) are bioactive lipids universally existing not only in human sera, but also in various organisms (Kobayashi, T., et al.:. Life Sci., 65, 2185-2191 (1999)).

Non-Patent Document 1: Murakarni-Murofushi, K., et al.: J. Biol. Chem., 267, 21512-21517 (1992)

Non-Patent Document 2: Murakami-Murofushi, K., et al.: Biochem. Biophys. Acta, 1258, 57-60 (1995)

Non-Patent Document 3: Kobayashi, T., et al.: Life Sci., 65, 2185-2191 (1999)

DISCLOSURE OF THE INVENTION

Object to be Achieved by the Invention

An object of the present invention is to elucidate an analgesic effect as one of new cPA bioactivities and thus to provide a novel analgesic agent.

Means for Attaining the Object

The present inventors have discovered cyclic phosphatidic acids (cPAs), which are bioactive phospholipids, from various eukaryotes and have studied for over dozen years concerning the physiological effects. Thus, the present inventors have discovered that cPAs have significant analgesic effects. Cyclic phosphatidic acids (cPAs) have analgesic effects equivalent to that of morphine as demonstrated by employed assays. Furthermore, cPAs are originally contained in living body, so that cPAs exhibit no toxicity or addiction when administered to living bodies from the outside, as revealed by animal experiments. The summary of the results of experiments concerning the effects of cPAs on the suppression of pain is as follows.

Specifically, the present inventors have examined the possibility of the intravenous administration of cPAs to induce analgesic effects using anesthetized rats with uninjured central nervous systems and two indicators: (1) heart rate increase reaction and (2) reflex potential in sympathetic cardiac branch, which are induced by electrical stimulation of hind limb afferent nerves. As a result, it could have been demonstrated by the two methods that cPAs clearly have analgesic effects and the effects may be exerted via an opioid receptor. In particular, first, the present inventors have applied electric pulse at a level at which rats feel pain, so as to induce rises in heart rate and examined possibility of suppression of rises in heart rate by cPA administration. Furthermore, the present inventors have exposed cardiac nerves and examined possibility of reduction (by cPA administration) in discharge levels induced by electric pulse using an experimental system for measurement of the discharge levels of nerve fibers. As a result, it has been demonstrated that cPAs suppress the discharge level in a dose-dependent manner and have high potential as an analgesic agent. The present invention has been completed based these findings.

The present invention provides an analgesic agent, which comprises a compound represented by the formula (1) as an active ingredient:

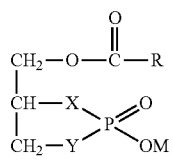

(1)

wherein R represents C1-30 linear or branched alkyl, C2-30 linear or branched alkenyl, or C2-30 linear or branched alkynyl, provided that such groups may optionally contain a cycloalkane ring or an aromatic ring; X and Y each independently represents —O— or —CH$_2$—, provided that X and Y do not simultaneously represent —CH$_2$—; and M represents a hydrogen atom or a counter cation.

Preferably, in the formula (1), X and Y represent —O—.

More preferably, in the formula (1), X or Y represents —CH$_2$—. The former is 2 carba cPA (abbreviated as 2ccPA), and the latter is 3 carba cPA (abbreviated as 3 ccPA). Particularly preferably, X is —CH$_2$— and Y is —O— (2 carba cPA).

Preferably, the compound represented by the formula (1) is 1-oleoyl cyclic phosphatidic acid or 1-palmitoleoyl cyclic phosphatidic acid.

Another aspect of the present invention provides a method for suppressing pain which comprises administering an effective amount of the compound represented by the aforementioned formula (1) to mammals including human beings.

Further another aspect of the present invention provides a use of the compound represented by the aforementioned formula (1) for the production of an analgesic agent.

Effects of the Invention

According to the present invention, it has been confirmed that a compound represented by the formula (1) has analgesic effects. Therefore, it has been revealed that the compound to be used in the present invention represented by the formula (1) is useful as an analgesic agent. According to the present invention, a novel analgesic agent is provided.

BEST MODES FOR CARRYING OUT THE INVENTION

The embodiments of the present invention will be described in detail below.

An analgesic agent of the present invention comprises a compound represented by the following formula (1) as an active ingredient.

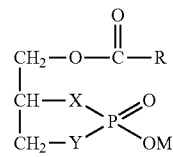

(1)

(wherein R represents C1-30 linear or branched alkyl, C2-30 linear or branched alkenyl, or C2-30 linear or branched alkynyl, provided that such groups may optionally contain a cycloalkane ring or an aromatic ring. X and Y each independently represents —O— or —CH$_2$—, provided that X and Y do not simultaneously represent M represents a hydrogen atom or a counter cation.)

In the formula (1), specific examples of C1-30 linear or branched alkyl represented by substituent R include methyl, ethyl, propyl, butyl, pentyl, hexyl, heptyl, octyl, nonyl, decyl, pentadecyl, and octadecyl.

Specific examples of C2-30 linear or branched alkenyl represented by substituent R include allyl, butenyl, octenyl, decenyl, dodecadienyl, and hexadecatrienyl and more specifically include 8-decenyl, 8-undecenyl, 8-dodecenyl, 8-tridecenyl, 8-tetradecenyl, 8-pentadecenyl, 8-hexadecenyl, 8-heptadecenyl, 8-octadecenyl, 8-icosenyl, 8-docosenyl, heptadeca-8,11-dienyl, heptadeca-8,11,14-trienyl, nonadeca-4,7,10,13-tetraenyl, nonadeca-4,7,10,13,16-pentaenyl, and henicosa-3,6,9,12,15,18-hexaenyl.

Specific examples of C2-30 linear or branched alkynyl represented by substituent. R include 8-decinyl, 8-undecinyl, 8-dodecinyl, 8-tridecinyl, 8-tetradecinyl, 8-pentadecinyl, 8-hexadecinyl, 8-heptadecinyl, 8-octadecinyl, 8-icocinyl, 8-docinyl, and heptadeca-8,11-diinyl.

Specific examples of a cycloalkane ring that can be contained in the above alkyl, alkenyl, or alkynyl include a cyclopropane ring, a cyclobutane ring, a cyclopentane ring, a cyclohexane ring, and a cyclooctane ring. A cycloalkane ring may contain one or more heteroatoms and examples of such a ring include an oxirane ring, an oxetane ring, a tetrahydrofuran ring, and a N-methylprolidine ring.

Specific examples of an aromatic ring that can be contained in the above alkyl, alkenyl, or alkynyl include a benzene ring, a naphthalene ring, a pyridine ring, a furan ring, and a thiophene ring.

Therefore, when substituent R represents an alkyl substituted with a cycloalkane ring, specific examples thereof include cyclopropylmethyl, cyclohexylethyl, and 8,9-methanopentadecyl.

When substituent R represents an alkyl substituted with an aromatic ring, specific examples thereof include benzyl, phenethyl, and p-pentylphenyloctyl.

X and Y in the compound represented by the formula (1) each independently represents —O— or —CH$_2$—, however, X and Y do not simultaneously represent —CH$_2$—.

Hence, the three combinations of X and Y are as follows.

(1) X represents —O— and Y represents —O—.
(2) X represents —CH$_2$— and Y represents —O—.
(3) X represents —O— and Y represents —CH$_2$—

M in a compound represented by the formula (1) represents a hydrogen atom or a counter cation. When M represents a counter cation, examples thereof include an alkaline metal atom, an alkaline-earth metal atom, a substituted or unsubstituted ammonium group. Examples of an alkaline metal atom include lithium, sodium, and potassium and examples of an alkaline-earth metal atom include magnesium and calcium. Examples of a substituted ammonium group include a butyl ammonium group, a triethyl ammonium group, and a tetramethyl ammonium group.

An example of cPAs represented by the formula (1), which is used in the present invention, is an oleoyl cPA (Ole-cPA) and particularly preferable examples of the same include a palmitoleoyl 2 carba cPA ($\Delta$Pal-2 ccPA) and a palmitoleoyl 3 carba cPA ($\Delta$Pal-3 ccPA).

A compound among compounds represented by the formula (1), in which X and Y each represents —O—, can be chemically synthesized according to the methods disclosed in JP Patent Publication (Kokai) No. 5-230088 A (1993), JP Patent Publication (Kokai) No. 7-149772 A (1995), JP Patent Publication (Kokai) No. 7-258278 A (1995), or JP Patent Publication (Kokai) No. 9-25235 A (1997), for example.

Furthermore, a compound among compounds represented by the formula (1), in which X and Y each represents —O—, can also be synthesized by reacting phospholipase D with lysophospholipids according to the method disclosed in JP Patent Publication (Kokai) No. 2001-178489 A. Lysophospholipids to be used herein are not particularly limited, as long as they are lysophospholipids that can react with phospholipase D. Many types of lysophospholipid are known, including those differing in fatty acid type and molecular species having an ether or vinylether bond. They are available in the market. As for phospholipase D, those derived from a higher plant such as cabbage, and peanut or from a microorganism such as *Streptomyces chromofuscus*, *Actinomadula* sp. are available in the market as commercial reagents. cPAs can be highly selectively synthesized with the enzyme derived from *Actinomadula* sp. No. 362 (JP Patent Publication (Kokai) No. 11-367032 A (1999)). Conditions for reaction between lysophospholipids and phospholipase D are not specifically limited, as long as an enzyme can exert its activity. The reaction of lysophospholipids with phospholipase D is carried out, for example, in an acetate buffer (around pH 5-6) containing calcium chloride at a temperature ranging from room temperature to a warmed temperature (preferably approximately 37° C.) for approximately 1 to 5 hours. The thus generated cPA derivative can be purified by extraction, column chromatography, thin-layer chromatography (TLC) or the like according to a conventional method.

Furthermore, a compound among compounds represented by the formula (1), in which X represents —CH$_2$— and Y represents —O—, can also be synthesized by the method disclosed in JP Patent Publication (Kokai) No. 2004-010582 A.

Furthermore, a compound among compounds represented by the formula (1), in which X represents —O— and Y represents —CH$_2$—, can be synthesized according to the method disclosed in the document (Kobayashi, S., et al., Tetrahedron Letters 34, 4047-4050 (1993); and "The Pharmaceutical Society of Japan, The 23$^{rd}$ Symposium of Advancement of Reaction and Synthesis, Nov. 17 and 18, 1997 (Kumamoto citizen hall), Synthesis and Physiological Effects of Cyclic Phosphatidic Acid and Carba Derivative, Summaries (pp. 101-104)) or the method disclosed in International Publication WO2002/094286. A specific example of the synthetic pathway is as follows.

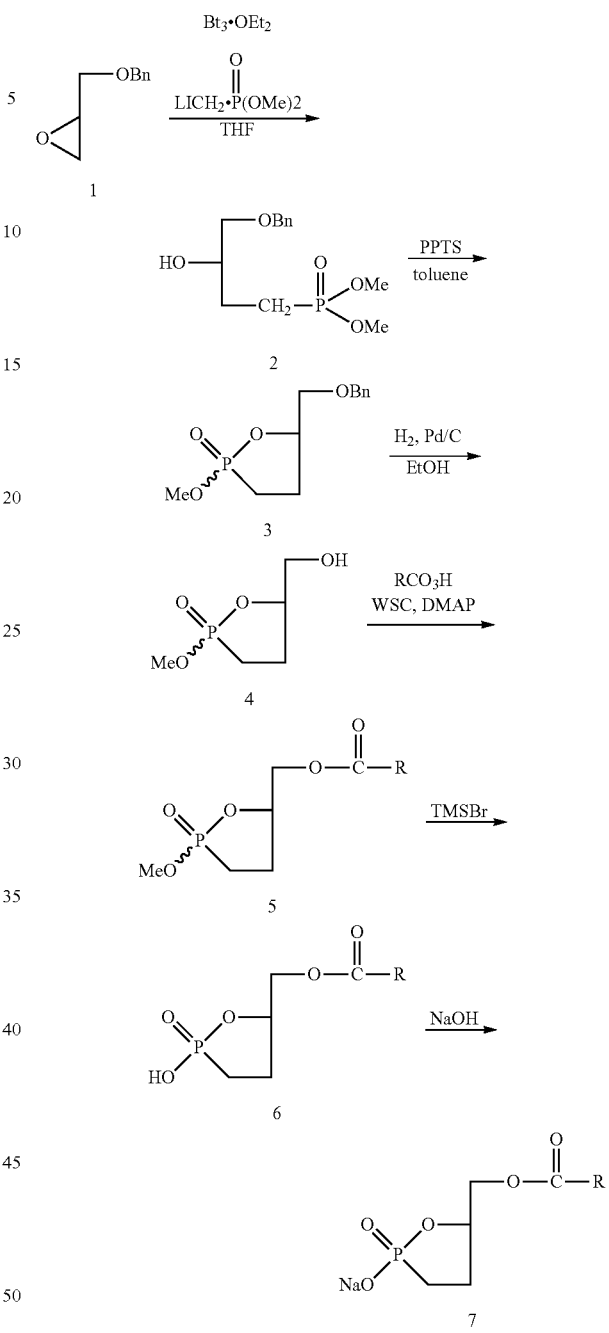

In the above synthetic pathway, first, commercially available (R)-benzylglycidyl ether (1) is activated, with BF$_3$.Et$_2$O followed by reaction with a lithio derivative obtained by reacting methyl phosphonic acid dimethyl ester with n-BuLi, so that alcohol (2) is obtained.

The thus obtained alcohol is reacted with an excess of a pyridinium salt of p-toluenesulfonic acid in toluene at 80° C., so that a cyclized product (3) is obtained. The cyclized product is decomposed with hydrogenation under a hydrogen atmosphere using 20% Pd(OH)$_2$—C, so that debenzylation is carried out (4). 1-ethyl-3-(3-dimethyl aminopropyl)carbodiimide hydrochloride as a condensation agent is reacted with fatty acid, so that a coupling product (5) is obtained. Next, bromotrimethyl silane is used as a nucleophile to position-selectively remove methyl groups alone, so that cyclic phosphonic acid (6) is obtained. The cyclic phosphonic acid (6) is transferred into a separatory funnel using ether, a small amount of a 0.02N sodium hydroxide aqueous solution is added dropwise, and then separation is carried out, so that a target compound is extracted and purified as a sodium salt (7).

Compounds represented by the formula (1) to be used as active ingredients' in the present invention have analgesic effects. Therefore, according to the present invention, an analgesic agent comprising such compound as an active ingredient is provided.

In the Example described below in the description, a method for evaluation of analgesic effects was employed. Specifically, possible exertion of analgesic effects due to intravenous administration of cPAs was examined using anesthetized rats with uninjured central nervous systems and indicators: (1.) heart rate increase reaction and (2) reflex potential in sympathetic cardiac branch, which are induced by electrical stimulation of hind limb afferent nerves. The two experimental systems used herein are basically according to the method of Uchida et al., (Neurosci Lett 269: 161, 1999) who have examined the effects of morphine.

Many methods are employed for examining the effects of analgesic substances, including a method for evaluation of the analgesic effects in humans and a method using as an indicator animals' escape behavior against various noxious stimuli such as tail pinching and heat. However, application of noxious stimuli to unanesthetized animals affects the emotion of the animals. Thus, quantitative evaluation of analgesic effects is difficult and the provision of agonies to animals raises an ethical issue.

Noxious stimuli can induce various reactions also in anesthetized animals. Such noxious stimuli activate peripheral nociceptive primary afferent nerve fibers, activate nociceptive neurons of the central nervous system, and can cause further various reflex reactions. Examples of well known reflex reactions under anesthesis include somatic kinetic reflex such as noxious flexion reflex, sympathetic reflex such as noxious pressor reflex, and endocrine reflex such as a noxious increase in blood catecholamine level.

Among (1) "heart rate increase reaction induced by frequent electrical stimulation of hindlimb afferent nerves" employed herein is not induced by weak stimulation intensity (0.2 V) that excites only thick medullated A-fibers, but induced by stimulation intensity (1 V) that is the same or higher than the excitation threshold of thin medullated A-fibers. When the stimulation intensity is further increased (10 V) so as to cause excitation of nonmedullated C fibers, the amplification of the heart rate increase reaction is increased to reach the maximum level (Sato et al, J Auton Nery Syst 4: 231, 1981; Uchida et al, Neurosci Left 269: 161, 1999). Noxious information is transmitted by A-fibers and C fibers. Therefore, such heart rate increase reaction induced by excitation of somatic afferent A-fibers and C fibers can be an indicator for evaluation of analgesic effects.

Among (2) "reflex potential induced by single electrical stimulation of hindlimb afferent nerves in sympathetic cardiac branch" employed herein, short latency A-reflex potential is induced and increased mainly by excitation of A-fibers. When the stimulation intensity is increased and nonmedullated C fibers are excited, delayed C-reflex potential is induced after induction of the above A-reflex potential (Ito et al, Neurosci Lett 39: 169, 1983; Adachi et al, Neurosci Res 15: 281, 1992).

C-reflex potential is specifically induced by the excitation of nonmedullated C fibers involved in transmission of noxious information, particularly burning delayed pain. Hence, a method using C-reflex potential as an indicator is excellent for evaluation of the action of analgesic agent. Among various types of pain, delayed pain that is transmitted by C fibers causes strong discomfort and thus is particularly important clinically. Sato et al., have demonstrated using this model for anesthetized cats that morphine selectively suppresses C-reflex potential alone and thus have reported that C-reflex potential induced by the excitation of somatic afferent C fibers can be an indicator for research concerning analgesic effects (see Pain Clinic 10 (5) 605, 1989). This method enables long-term stable measurement and enables continuous examination of the effects by minutes, so that this method is also excellent in evaluation of the time courses of drug effects.

Meanwhile, regarding A-reflex potential, reflex due to stimulation A-fibers (among medullated nerve fibers) involved in transmission of noxious information overlaps reflex due to A-fibers. Hence, examination of the effects of drugs on reflexes due to only A-fibers involved in sharp and rapid pain is difficult.

Anesthetized animals are used in both methods employed herein. Accordingly, the methods are advantageous such that noxious stimuli can be applied without causing pain and specific reflexes induced by noxious stimuli can be examined. Thus, the methods can create models for evaluation of analgesic effects as objective measurement methods.

The analgesic agent of the present invention is preferably provided in the form of a pharmaceutical composition containing 1, 2, or more pharmaceutically acceptable pharmaceutical additives and a compound represented by the formula (1), which is an active ingredient.

The analgesic agent of the present invention can be administered in various forms. An appropriate form of administration may be either oral administration or parenteral administration (e.g., intravenous, intramuscular, subcutaneous, or intradermal injection, intrarectal administration, and transmucosal administration). Examples of pharmaceutical compositions appropriate for oral administration include tablets, fine granules, capsules, powders, solutions, suspensions, and syrups. Examples of pharmaceutical compositions appropriate for parenteral administration include injections, infusions, suppositories, and transdermal absorption systems. However, the dosage forms of the analgesic agent of the present invention are not limited to these examples. Moreover, the analgesic agent of the present invention can be produced in the form of prolonged action preparation by known technology.

Types of pharmaceutical additives to be used for production of the analgesic agent of the present invention are not particularly limited and can be adequately selected by persons skilled in the art. For example, excipients, disintegrators or disintegration adjuvants, binders, lubricants, coating agents, bases, solubilizing agents or solubilization adjuvants, dispersants, suspensions, emulsifiers, buffers, antioxidants, antiseptics, isotonizing agents, pH-adjusting agents, lytic agents, and stabilizers can be used. Specific individual ingredients to be used for these purposes are known by persons skilled in the art.

Examples of pharmaceutical additives that can be used for preparation of pharmaceutical preparations for oral administration include: excipients such as glucose, lactose, D-mannitol, starch, and crystalline cellulose; disintegrators or disintegration adjuvants such as carboxymethyl cellulose, starch, and carboxymethyl cellulose calcium; binders such as hydroxy propyl cellulose, hydroxy propyl methyl cellulose, polyvinylpyrrolidone, and gelatin; lubricants such as magnesium stearate and talc; coating agents such as hydroxy propyl methyl cellulose, saccharose, polyethylene glycol, and titanium oxide; and bases such as Vaseline, liquid paraffin, polyethylene glycol, gelatin, kaoline, glycerin, purified water, and hard fat.

Examples of pharmaceutical additives that can be used for preparation of pharmaceutical preparations for injection or drip infusion include: solubilizing agents or solubilization adjuvants that can compose aqueous injections or injections that are dissolved upon use, such as distilled water for injection, a physiological saline solution, and propylene glycol; isotonizing agents such as glucose, sodium chloride, D-mannitol, and glycerine; pH adjusting agents such as inorganic acid, organic acid, inorganic base, and organic base.

The analgesic agent of the present invention can be administered to mammals including humans.

The dose of the analgesic agent of the present invention should be adequately increased or decreased depending on conditions of a patient's age, sex, body weight, and symptoms, and the route of administration, for example. Generally the amount of an active ingredient per day for an adult ranges from approximately 1 µg/kg to 1,000 mg/kg and preferably ranges from approximately 10 µg/kg to 100 mg/kg. The above dose of the analgesic agent may be administered once a day or at several separate times (e.g., approximately 2 to 4 times).

The analgesic agent of the present invention can also be used in combination with other analgesic agent and the like.

In addition, cPAs themselves that are active ingredients of the present invention are substances existing in the mammalian sera, brains, or the like. Hence, cPAs are thought to be safe for organisms.

The present invention is described more specifically with reference to the following Examples, but is not limited to these Examples.

Example (1) Experimental Methods

Biological Materials

Wister male rats (body weight: 300 g-375 g) were used.

Anesthesia

Urethane (1.1 g/Kg) was initially administered intraperitoneally to rats and then the rats were anesthetized. Anesthetic depth was observed based on changes in blood pressure and heart rate, and then urethane was subcutaneously administered every 1 to 2 hours in an amount ½0 to ⅟10 the initial dose, so that anesthetic depth was maintained.

Maintenance of Respiration

The trachea of each rat was cut open, a tracheal cannula was inserted, and then respiration was maintained using an artificial respirator (SN-480-7, Shinano, Tokyo). The carbon dioxide concentration in expired air was monitored using an expired gas monitor (1H26, NEC San-ei, Tokyo), and the respiratory volume was regulated to be approximately 3% during the experiment.

Maintenance of Body Temperature

A thermister was inserted rectally. The core temperature was constantly monitored using a body temperature control device (ATB-1100, Nihon kohden) so that the body temperature was maintained at 37.5° C.

Measurement of Blood Pressure-Fluid Replacement

The right femoral artery was cannulated. Arterial blood pressure was continuously recorded from the intra-arterial cannula using a pressure transducer (TP-400T, Nihon Kohden, Tokyo).

Measurement of Heart Rate

Blood pressure waveform was collected using a pulse rate tachometer (AT601-O, Nihon Kohden) and the heart rate was recorded continuously.

Record of Sympathetic Cardiac Branch Activity

Left second rib was removed, in the supine position. Left sympathetic cardiac branch running from the stellate ganglion to the heart was separated and dissected at a position as close as possible to the heart. Nerves were immersed in paraffin oil so as not to be dried. Separated nerve center ends were placed on a platinum iridium electrode. Efferent nerve activity of the sympathetic cardiac branch was derived and then amplified using an amplifier (S-0476, Nihon Kohden, time constant 0.33 s). The result of reflex reaction induced by electrical stimulation of hindlimb afferent nerves was added 50 times with an adder (ATAC3700, Nihon Kohden). The averaged reaction results were displayed on the screen and then recorded on a mini writer. The size of reflex reaction was evaluated via measurement of the area of the thus induced reaction and the result was expressed with % with respect to the size of the control (before cPA administration). At the time of recording sympathetic nerve activity, a muscle relaxant, gallamine triethiodide (20 mg/kg, i.v.), was administered to avoid body motion that could block stable recording of nerve activity.

Electrical Stimulation of Hindlimb Afferent Nerves

Left tibial nerves were dissected from the peripheral tissue. The dissected center end was placed on a stimulating electrode and then electrically stimulated by a supramaximal square-wave pulse (pulse width: 0.5 ins and intensity: 10-20V) using an electric stimulator (SEN-7103, Nihon Kohden). In an experiment for examining heart rate increase reaction, frequent electrical stimulation (10 Hz) was applied for 5 seconds. In an experiment of reflex potentials, single electrical stimulation was applied every 3 seconds.

Preparation and Administration of cPAs

Products chemically synthesized according to the method disclosed in Kobayashi, S., et al.: Tetrahedron Lett., 34, 4047-4050 (1993) or products enzymatically synthesized according to the method disclosed in JP Patent Publication (Kokai) No. 2001-178489 A were used as Pal-cPA (16:0) (palmitic acid is bound at position sn-1), ΔPal-cPA (16:1) (palmitoleic acid is bound at position sn-1) and Ole-cPA (18:1) (oleic acid is bound at position sn-1). There are no differences in terms of effects between purified chemically-synthesized products and enzymatically-synthesized products.

2 carba and 3 carba derivatives were synthesized according to the method disclosed in JP Patent Publication (Kokai) No. 2004-010582 and the method disclosed in International Publication WO2002/094286, respectively.

Crystals were dissolved in ethanol and then evaporated to dryness in the form of film using a nitrogen gas. The resultant was dissolved in a physiological saline solution (0.9% NaCl) immediately before administration, so that a 2.5 mg/mL or 0.5 mg/mL solution was prepared.

Each cPA was, administered intravenously via the cannula inserted in the right femoral vein. When the dose was less than 1 mg/Kg body weight, a 0.5 mg/mL solution was injected and when the dose was 1 mg/Kg body weight or more, a 2.5 mg/mL solution was injected. Injection rate was 150 mL/minute in both cases.

(2) Results and Discussion

Effects of cPAs on Heart Rate Increase

The suppressive effect of Ole-cPA administration on heart rate increase was verified using two 2 rats. The suppressive effect was observed when the dose was mg/Kg body weight or more and observed to increase in a concentration-dependent manner (FIG. 1). When the dose was 5 mg/Kg body weight, the heart rate increase was found to be a half of or lower than that of the control. Regarding the duration of the suppressive effect, the suppressive effect was confirmed even at 20 minutes after administration when the dose was higher than 1 mg/Kg body weight. The suppressive effect was then observed to increase in a concentration-dependent manner. In the case of 5 mg/Kg, the significant suppressive effect was observed even after 20 minutes. As described above, it was demonstrated that heart rate increase that is induced by electrical stimulation of lower extremity nerves is significantly suppressed by administration of Ole-cPA.

On the other hand, in the case of administration of Pal-cPA, the suppressive effect on heart rate increase could be confirmed on the whole, however, no consistent tendency could be confirmed.

Effects of cPA Administration on Blood Pressure

The effects of cPA administration on blood pressure were examined using 2 rats simultaneously with the examination of the suppressive effect on heart rate increase. When the dose of Ole-cPA was 2 mg/Kg body weight or less, the blood pressure almost remained unchanged at 90 mmHg and the effects due to administration was not observed. On the other hand, when the dose of Pal-cPA was 300 μg/Kg body weight, the blood pressure was found to briefly increase to around 100 mmHg; and after administration of the dose of 2 mg/Kg body weight, the blood pressure was found to increase to 130 mmHg. Then the blood pressure remained unchanged at around 130 mmHg and no decrease in blood pressure was confirmed even at 30 minutes after administration.

Changes in Discharge Levels of Cardiac Nerves Due to cPA Administration

Measurement of the discharge levels of cardiac nerves was verified using 4 rats. The suppressive effect of cPAs on heart rate increase due to stimulation was significantly observed in the case of Ole-cPA, but was not significant in the case of Pal-cPA. Hence, changes in the discharge levels of cardiac nerves due to stimulation were examined only in the case of Ole-cPA. FIG. 2 shows typical electrograms obtained before cPA administration and after administration. Particularly the level of C reflex decreased by cPA administration.

FIG. 3 shows changes with time in discharge levels after cPA administration. Here, discharge levels (peak areas in FIG. 2) are expressed with relative values obtained via normalization with the use of the level before cPA administration. At any concentrations, the discharge level of C reflex was found to decrease by up to 40% (approximately 1 mV) at 10 to 15 minutes after administration. The discharge level was observed to increase again after 20 to 25 minutes. However, when the dose was 2 mg/Kg, a state of a decrease by approximately 20% (compared with that before administration) was maintained even at 30 minutes after administration. The time course of the suppressed discharge level after cPA administration was almost in agreement with, that observed upon suppression of heart rate increase. Furthermore, dose dependency similar to that observed in the case of the suppressive effect on heart rate increase was observed in the case of the suppression level.

Meanwhile, in the case of Aδ reflex, changes were observed in the discharge level after cPA administration, however, the changes were observed to be inconsistent compared with C reflex. Furthermore, a consistent change in the case of C reflex was observed for 4 rats used in the experiment, whereas changes in the discharge level of Aδ reflex were thought to have properties easily affected by individual differences or physiological conditions.

The effects of 2 carba cPAs (Ole-, Pal-, and ⊿Pal-) and 3 carba cPAs (Ole-, Pal-, and ⊿Pal-) on heart rate, blood pressure, the discharge level of cardiac nerve were examined by a method similar to that employed for a natural cPA.

Regarding the effects on heart rate, the suppressive effect of Ole-cPA and the same of ⊿Pal-carba cPA on heart rate increase were observed at levels almost the same as that of a natural Ole-cPA.

Regarding the effects on blood pressure, similar to Ole-cPA, no effects due to administration were observed in all cases.

In the case of administration of palmitoleoyl 2 carba cPA (⊿Pal-2 ccPA) among 2 carba cPAs, a significant decrease was observed in the depolarization level of cardiac nerves and particularly of C reflex.

The effect of ⊿Pal-2 ccPA with a concentration ranging from 50 μg/Kg to 500 μg/Kg on the depolarization level of C reflex was analyzed. As a result, at any concentration, the depolarization level of C reflex was found to decrease at 10 to 15 minutes after administration. Specifically, an approximately 30% or more decrease was observed when the concentration was 50 μg/Kg (1/40 of the concentration (2 mg/Kg) at which natural Ole-cPA causes an approximately 50% decrease), an approximately 60% decrease was observed when the concentration was 100 μg/Kg (1/20 of the same), an approximately 70% decrease was observed when the concentration was 200 μg/Kg (1/10 of the same), and an approximately 80% decrease was observed when the concentration was 500 μg/Kg (1/4 of the same). The depolarization level was observed to increase again after 20 to 25 minutes, and then observed to gradually return to the level at the time of administration.

In the case of administration of palmitoleoyl 3 carba cPA (⊿Pal-3 ccPA) among 3 carba cPAs, a significant decrease was observed in the depolarization level of cardiac nerves and particularly of C reflex, similarly to 2 carba derivatives. The degree of the decrease was somewhat lower than those of 2 carba derivatives. The depolarization level of C reflex was found to decrease at 10 to 15 minutes after administration of ⊿Pal-3 ccPA with a concentration ranging from 50 μg/Kg to 200 μg/Kg. An approximately 30% decrease was observed when the concentration was 50 μg/Kg (1/40 of the concentration (2 mg/Kg) at which natural Ole-cPA causes an approximately 50% decrease), an approximately 50% decrease was observed when the concentration was 100 μg/Kg (1/20 of the same), and an approximately 60% decrease was observed when the concentration was 200 μg/Kg (1/10 of the same). Also in this case, the depolarization level was observed to increase again after 20 to 25 minutes and then gradually return to the level at the time of administration.

FIG. 4 shows comparison of Ole-cPA, ⊿Pal-2 ccPA, and ⊿Pal-3 ccPA.

The results are as described above such that heart rate increase and depolarization of cardiac nerves due to electrical stimulation were lowered by administration of a cPA, 2 ccPA, or 3 ccPA. The depolarization level of C reflex is thought to reflect chronic pain. The results strongly suggest that cPAs and derivatives thereof, 2 ccPA and 3 ccPA, have significant analgesic effects.

Expected Mechanisms of Analgesic Effects Exerted by cPAs

The following action mechanisms of the analgesic effects exerted by cPAs are expected.

(1) Evaluation is made using reactions due to electrical stimulation of afferent nerve fibers on the central side from the nociceptor, so as to eliminate the possibility that the effects are peripheral effects on the periphery of the nociceptor.

(2) Transmission of excitation in primary afferent C fibers may be blocked.

(3) Nociceptive transmitter release within the central nerve, such as glutamate or substance P release from primary afferent C fiber ends in the posterior horn of the spinal cord, may be suppressed.

(4) Within the central nerve, such as within the posterior horn of the spinal cord, an opioid analgesic system may be activated by the effect of accelerating endogenous opioid release or the effect of increasing opioid receptor sensitivity.

(5) A nonopioid analgesic system such as a serotoninergic descending inhibitory system, a noradrenergic descending inhibitory system, or a GABA-mediated analgesic system may be activated.

(6) The analgesic effects may be antagonistic to the pain generation effects of LPA.

Figure 1:
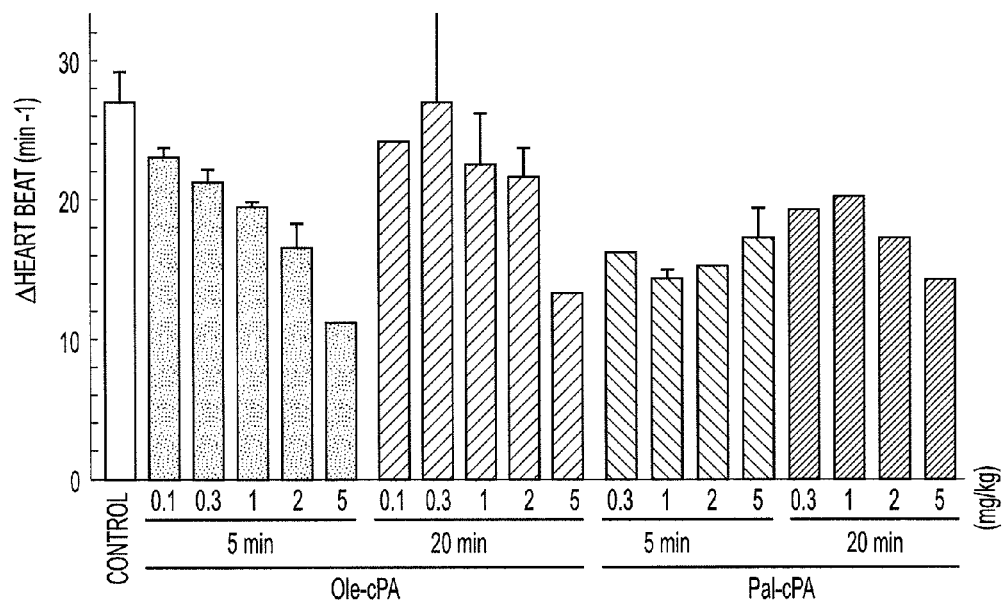
FIG. 1 shows the effects of the administration of cPAs on changes in heart rate after stimulation of lower extremity nerves.
Figure 2:
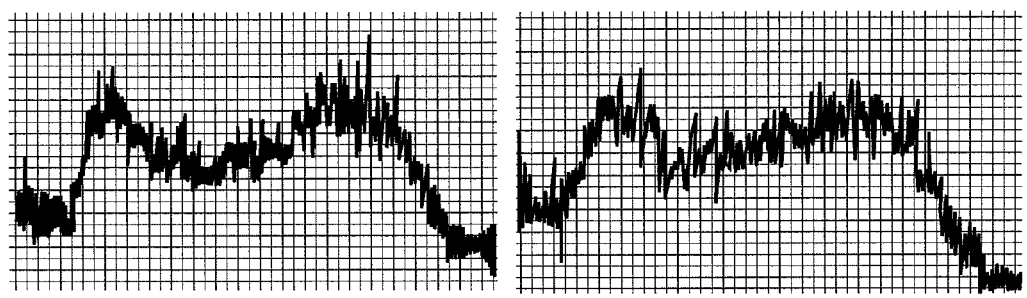
FIG. 2 shows representative examples of the electrogram obtained before administration of a cPA (left) and the same obtained after administration (right). Peaks on the left and the right represent Aδ reflex and C reflex, respectively.
Figure 3A:
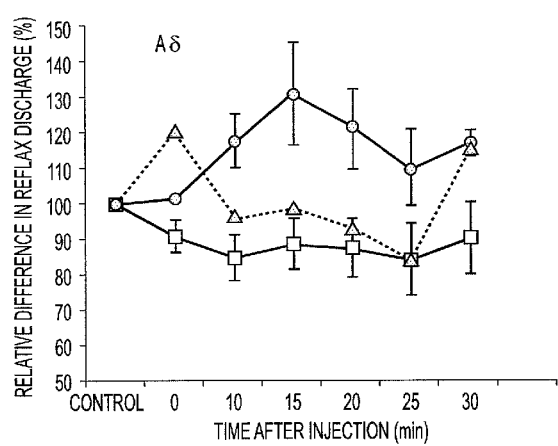
FIG. 3 shows changes in Aδ and C reflex levels of cardiac nerves after stimulation of lower extremity nerves. Each data point represents an average value calculated every 5 minutes. Response levels obtained with 2 to 3 instances of administration to each rat were averaged. The thus obtained average response levels were further averaged for 4 rats. The bar denotes the standard error.
Figure 3B:
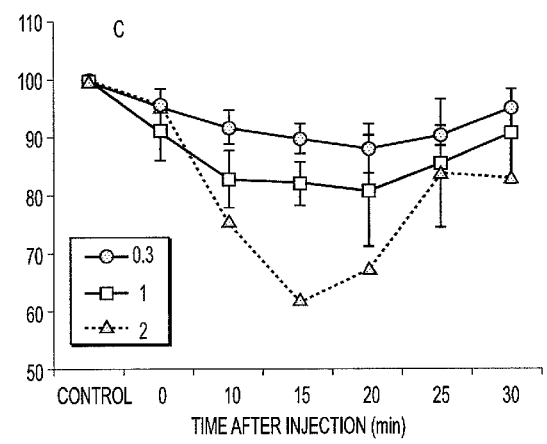
Figure 4:
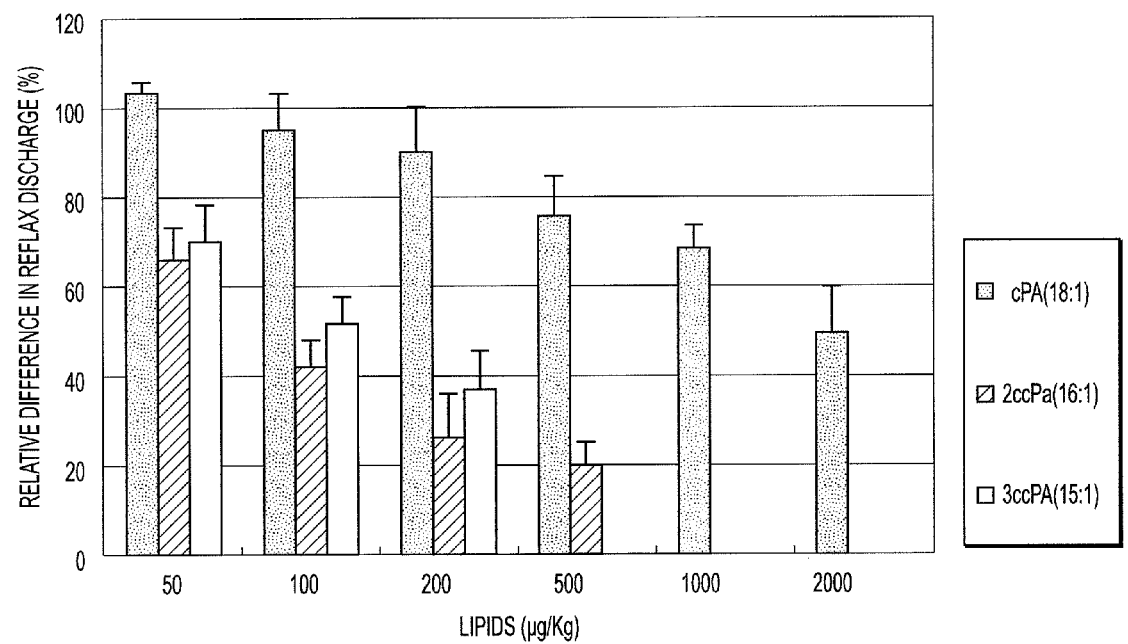
FIG. 4 shows the results of comparing the effects of natural Ole-cPA with the effects (changes in C reflex levels of cardiac nerves after stimulation of lower extremity nerves by administration of ΔPal-2 ccPA or ΔPal-3 ccPA having varied concentrations (μg/Kg)) of ΔPal-2 ccPA or ΔPal-3 ccPA. The peak area of C reflex was measured and the result was used for the depolarization level for each reflex. In each administration, the depolarization level immediately before administration (0 minute) was used as the standard and then a relative depolarization level (%) was calculated. The graph shows average values of relative depolarization levels measured at 10 to 15 minutes after administration.

What is claimed is:

1. A method of alleviating pain comprising administering an effective amount to a patient in need thereof, a compound represented by the formula (1):

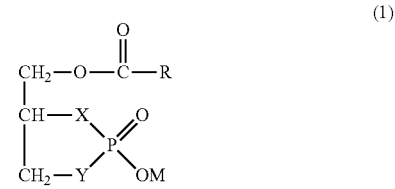

wherein R represents $C_1$-$C_{30}$ linear or branched alkyl, $C_2$-$C_{30}$ linear or branched alkenyl, or $C_2$-$C_{30}$ linear or branched alkynl, provided that such groups are optionally substituted by a cycloalkane ring or an aromatic ring; X and Y each independently represents —O— or —$C_2$—, provided that X and Y do not simultaneously represent —$CH_2$—; and M represents a hydrogen atom or a counter cation, or a pharmacologically acceptable salt thereof, to alleviate pain.

2. The method according to claim 1, wherein in the compound of formula (1), X and Y represent —O—.

3. The method according to claim 1, wherein in the compound of formula (1), X X or Y represents —$CH_2$—.

4. The method according to claim 1, wherein the compound of formula (1) is 1-oleoyl cyclic phosphatidic acid or 1-palmitoleoyl cyclic phosphatidic acid.

* * * * *

UNITED STATES PATENT AND TRADEMARK OFFICE
CERTIFICATE OF CORRECTION

| | | |
|---|---|---|
| PATENT NO. | : 8,017,597 B2 | Page 1 of 1 |
| APPLICATION NO. | : 12/907666 | |
| DATED | : September 13, 2011 | |
| INVENTOR(S) | : Murofushi et al. | |

It is certified that error appears in the above-identified patent and that said Letters Patent is hereby corrected as shown below:

Column 14, Line 35, in Claim 3, Line 2, "X X or Y" should be --X or Y--.

Signed and Sealed this
Third Day of April, 2012

David J. Kappos
*Director of the United States Patent and Trademark Office*